(12) United States Patent
Leeuwenburgh

(10) Patent No.: US 6,541,265 B2
(45) Date of Patent: Apr. 1, 2003

(54) METHOD AND SYSTEM TO TEST A SUBSTANCE FOR INFLAMMATORY OR OXIDANT PROPERTIES

(75) Inventor: Christiaan Leeuwenburgh, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/852,194

(22) Filed: May 9, 2001

(65) Prior Publication Data

US 2003/0044878 A1 Mar. 6, 2003

(51) Int. Cl.[7] .............................................. G01N 33/00
(52) U.S. Cl. .............................. 436/86; 436/74; 436/84
(58) Field of Search ............................. 436/63, 73, 74, 436/84, 904, 86

(56) References Cited

U.S. PATENT DOCUMENTS

| | | | |
|---|---|---|---|
| 4,741,530 A | 5/1988 | Wolf | |
| 4,765,610 A | 8/1988 | Sidwell | |
| 5,827,154 A | 10/1998 | Gill | |
| 6,146,351 A | * 11/2000 | Kempe | ........................ 128/846 |

OTHER PUBLICATIONS

Childs, A. et al. "Vitamin C and N–acetyl–cysteine supplementation increases oxidative stress in humans after eccentric muscle injury" Poster Session–Oxygen Society Meeting (Nov., 2000), San Diego, California.

Croisier, J–L. et al. "Piroxicam fails to reduce myocellular enzyme leakage and delayed onset muscle soreness induced by isokinetic eccentric exercise" *Mediators of Inflammation* (1996), pp. 230–234 vol. 5(3), Rapid Science Publishers.

Jenkins, R. R. et al. "Influence of exercise on clearance of oxidant stress products and loosely bound iron" *Medicine and Science in Sports and Exercise* (1993), pp. 213–217, vol. 25(2).

Leeuwenburgh, C., LI LI JI "Alteration of glutathione and antioxidant status with exercise in unfed and refed rats" *J. Nutrition* (1996), pp. 1833–1843, vol. 126.

Roginsky, Vitaly A., Hartmut B. Stegmann "Ascorbyl radical as natural indicator of oxidative stress: quantitative regularities" *Free Radical Biology and Medicine* (1994), pp. 93–103, vol. 7(2).

Leeuwenburgh, C. et al. "Aging and exercise training in skeletal muscle: responses of glutathione and antioxidant enzyme systems" *Am. J. Physiol.* (1994), pp. R439–445, vol. 267.

Burgeois, J. et al. "Naproxen does not alter indices of muscle damage in resistance–exercise trained men" *Medicine and Science in Sports and Exercise* (1999) pp. 4–9, vol. 31(1).

Child, R. et al. "Changes in plasma indices of antioxidant status, lipid peroxidation and inflammation in human skeletal muscle after eccentric muscle actions" *Clinical Science* (1999) pp. 105–115, vol. 96.

Maxwell, S. R. et al. "Changes in plasma antioxidant status during eccentric exercise and the effect of vitamin supplementation" *Free Rad. Res. Comms.* (1993) pp. 191–202, vol. 19(3), Harwood Academic Publishers GmbH, U.S.A.

Van Der Meulen, J. et al. "Contraction–induced injury to the extensor *digitorum longus* muscles of rats: the role of vitamin E" *J. Appl. Physiol.* (1997) pp. 817–823, vol. 83(3).

Pizza, F. X. et al. "Anti–inflammatory does of ibuprofen: effect on neutrophils and exercise–induced muscle injury" *Int. J. Sports Medicine* (1999) pp. 98–102, vol. 20.

Halliwell, B. et al. *Free Radicals in Biology and Medicine* (1999), pp. 200–208, Oxford University Press, New York.

* cited by examiner

*Primary Examiner*—Maureen M. Wallenhorst
(74) *Attorney, Agent, or Firm*—Saliwanchik, Lloyd & Saliwanchik

(57) ABSTRACT

The subject invention pertains to methods and systems for testing a substance for inflammatory or oxidant properties under acute inflammatory conditions characterized by increased levels of redox-active metal ions. The method includes the steps of applying an eccentric exercise stimulus to a subject, thereby inducing a muscle injury; administering a substance of interest to the subject; measuring one or more biological markers of inflammation, oxidative stress, and muscle damage, or combinations thereof, within the subject; and correlating the measured value of the biological marker (s) with the inflammatory or oxidative properties of the substance administered. The systems of the subject invention include means for obtaining a biological sample from a subject, means for applying eccentric exercise stimulus to the subject; means for measuring the amount of the biological marker(s) within the biological sample; and means for correlating the measured amounts of the biological marker (s) with the inflammatory or oxidant properties of the substance administered.

45 Claims, 4 Drawing Sheets

METHOD AND SYSTEM TO TEST A SUBSTANCE FOR INFLAMMATORY OR OXIDANT PROPERTIES

BACKGROUND OF THE INVENTION

The consumption of foods rich in antioxidant compounds is well known to reduce the incidence of many chronic disease states, such as cancer. Moreover, the intake of certain antioxidants, such as vitamins C (ascorbic acid) and E (α-tocopherol), is essential for survival in humans and most mammals, because these compounds are not biosynthesized.

Aerobic organisms are partially protected against oxidative challenges by sophisticated antioxidant defense systems. The importance of antioxidant defense systems in humans is demonstrated by the essential in vivo presence of both enzymatic and non-enzymatic antioxidant components. Oxidative stress and resultant oxidative damage may occur as a result of oxidative challenges such as air pollution or the "oxidative burst" associated with activated neutrophils mediated by the immune response. A constant source of oxidative stress results from formation of superoxide anions via "electron leakage" in the mitochondria during production of adenosine triphosphate (ATP). Although a superoxide anion is not exceedingly reactive in and of itself, it can initiate a cascade of events that eventually results in the formation of highly reactive free radicals and other oxidants. If these reactive oxygen species are not controlled by enzymatic and/or non-enzymatic antioxidant systems, in vivo oxidation of critical cellular components such as membranes, DNA, and proteins will result, eventually leading to tissue damage and dysfunction.

Inflammation can be induced by acute exercise in untrained individuals (Jenkins, R. R. et al. [1993] *Med Sci Sports Exerc* 25:213–7). Strenuous exercise increases oxygen consumption and causes disturbance of the intracellular homeostasis between pro-oxidants and antioxidant, resulting in oxidative stress. Reactive oxygen species pose a serious threat to the cellular antioxidant defense system, such as by diminishing the reserve of antioxidant vitamins and glutathione, and increasing tissue susceptibility to oxidative damage. However, enzymatic and non-enzymatic antioxidants have demonstrated great adaptation to acute and chronic exercise. The delicate balance between pro-oxidants and antioxidants suggests that supplementation of antioxidants may be desirable for physically active individuals under certain physiological conditions by providing a larger protective margin.

In vitro experiments have shown that certain substances, including some antioxidant vitamins, such as vitamin C, are reactive with free iron and can cause oxidative damage to biomolecules. Under normal physiological conditions, metals are found bound to circulating proteins and rendered redox-inactive (Halliwell, B. et al. [1999] *Free radicals in Biology and Medicine*. Oxford N.Y.: Clarendon Press, Oxford University Press; Winterboum, C. C. [1981] *Biochem J* 198:125–31). However, levels of free metals, such as iron, may be elevated during acute inflammation and become redox-active. Others have shown that under several physiological and pathophysiological conditions, increases in free iron in the presence of vitamin C results in oxidative stress.

Inflammation stimulates polymorphonuclear leukocytes and macrophages that produce large amounts of superoxide ($O_2^{\cdot-}$) and hydrogen peroxide ($H_2O_2$) (Babior, B. M. et al. [1973] *J Clin Invest* 52:741–744; Halliwell, B., et al. [1999] supra). The detrimental effects of these radicals may be amplified in the presence of iron and the subsequent formation of other reactive intermediates, such as the hydroxyl radical ($HO^\cdot$). NADPH oxidase, a membrane-associated electron transport chain protein, becomes activated during inflammation and directly reduces $O_2$ to $O_2^{\cdot-}$ (Equation 1). Superoxide can then be dismutated by superoxide dismutase to produce $H_2O_2$ (Equation 2).

$$NADPH + 2O_2 \rightarrow 2O_2^{\cdot-} + NADP^+ + H^+ \quad \text{(Equation 1)}$$

$$O_2^{\cdot-} + O_2^{\cdot-} + 2H^+ \rightarrow H_2O_2 + O_2 \quad \text{(Equation 2)}$$

Superoxide can reduce transition metals, including ferric iron ($Fe^{3+}$), to ferrous iron ($Fe^{2+}$) (Equation 3). The reduced metal ion can then react with $H_2O_2$ to generate the highly oxidizing $HO^\cdot$ radical species (Equation 4).

$$Fe^{3+} + O_2^{\cdot-} \rightarrow O_2 + Fe^{2+} \quad \text{(Equation 3)}$$

$$Fe^{2+} + H_2O_2 \rightarrow HO^\cdot + OH^- + Fe^{3+} \quad \text{(Equation 4)}$$

The hydroxyl radical has been widely postulated to cause significant damage to several biomolecules in vivo. Although the relevance of the hydroxyl radical in biology has been questioned because of the requirement of redox-active free iron, Biemond and colleagues have shown iron release from ferritin during inflammation (Biemond, P. et al. [1984] *J Clin Invest* 73(6): 1576–9).

In vitro vitamin C can exert pro-oxidant effects. The reduction potentials of $Fe^{3+}$ (−0.4 V) and ascorbate (−0.17 V) easily allow the formation of the ascorbate radical and $Fe^{2+}$ iron (Equation 5).

$$Fe^{3+} + \text{ascorbate} \rightarrow Fe^{2+} + \text{ascorbate}^\cdot \quad \text{(Equation 5)}$$

In addition, the formation of ferrous iron increases the possibility of the production of $HO^\cdot$ by reacting with $H_2O_2$ (Equation 4). Thus, it is feasible that the release of iron and the presence of vitamin C during acute inflammation characterized by high fluxes of oxidants could lead to $HO^\cdot$ and ascorbate generation.

The reduction potentials of $Fe^{3+}$ (−0.4 V) and ascorbate (−0.17 V) easily allow the formation of the ascorbate radical and $Fe^{2+}$ iron (Equation 5). Therefore, in vitro vitamin C can exert pro-oxidant effects, by converting $Fe^{3+}$ into $Fe^{2+}$, which reacts with $H_2O_2$ to generate $HO^\cdot$ (Halliwell, B. et al. [1999] supra; Roginsky, V. A. et al. [1994] *Free Radic Biol Med* 17:93–103). Iron-ascorbate mixtures have been shown to stimulate free-radical damage to DNA, lipids, and proteins in vitro (Halliwell, B. et al. [1990] *Methods Enzymol* 186:1–85). In vivo iron (Kadiiska, M. B. et al. [1995] *J Clin Invest* 96:1653–7) supplementation and ascorbate-copper supplementation (Kadiiska, M. B. et al. [1992] *Mol Pharmacol* 42:723–9) to rats have been reported to stimulate $HO^\cdot$ generation. Thus, it is feasible that the release of iron and the presence of vitamin C during acute inflammation could lead to $HO^\cdot$ and ascorbate$^\cdot$ generation.

Until recently, there has been no investigation as to whether antioxidant supplements can act as pro-oxidants, causing oxidative stress in humans or animals under acute inflammatory conditions characterized by increases in levels of redox-active metal ions. Long-term supplementation with these compounds could have detrimental effects in patients suffering from acute inflammation and inflammatory conditions accompanied by increased levels of free iron. However, these supplements could also have detrimental effects on patients with certain disease conditions characterized by increased levels of free iron without the presence of inflammation. Such disease conditions include, for example, Alzheimer's, Parkinson's, atherosclerosis, diabetes, and hemachromotosis (Gerlach, M. et al. [1994] *J Neurochem* 63(3):793–807; Halliwell, B. et al. [1985] *Mol Aspects Med* 8(2):89–193). One study protective effect of vitamin C in the plasma in the presence of high levels of free iron in vitro, without the presence of inflammation (Berger, T. M. et al. [1997] *J Biol Chem* 272: 15656–60). The Berger study (Berger, T. M. et al. [1997] supra) investigated if the naturally occurring high levels of ascorbic acid in pre-term infants, along with the presence of detectable levels of iron, would increase oxidative stress. The Berger study showed no concurrent increases in either lipid hydroperoxides or protein carbonyls in the plasma of these infants. In contrast, others suggest that co-supplementing healthy volunteers with iron and vitamin C increased levels of oxidative DNA damage in white blood cells. It was concluded that increased levels of DNA damage in well-nourished subjects after iron/ascorbate supplementation are disturbing in view of the frequent use of dietary supplements containing both iron salts and ascorbate (Bolann, B. J. et al. [1990] *Eur J Biochem* 193:899–904; Rehman et al [1998] *Biochem Biophys Res Commun* 246:293–8).

Inflammation can be induced by prolonged or damaging exercise and can increase the levels of free iron (Jenkins, R. R. et al. [1993] supra). Part of the inflammatory reaction to muscle injury includes a systemic response in addition to the changes observed locally at the muscle. Several types of exercises damage enzymes and lipid membranes, increase DNA damage, stimulate oxidative stress, and increase plasma markers of cell damage (Jenkins, R. R. et al. [1993] supra; Camus, G. et al. [1994] *Arch Int Physiol Biochim Biophys* 102:67–70; Fielding, R. A. et al. [2000] *Med Sci Sports Exerc* 32:359–64; Ji, L. L. [1995] *Exerc Sport Sci Rev* 23:135–66; Leeuwenburgh, C. et al. [1999] *Free Radic Biol Med* 27:186–92; MacIntyre, D. L. et al. [2000] *Eur J Appl Physiol* 81:47–53; Maughan, R. J. et al. [1989] *Muscle Nerve* 12:332–6; Powers, S. K. et al. [1999] *Med Sci Sports Exerc* 31:987–97).

Eccentric exercise is a particularly damaging activity involving forced lengthening of a muscle as it develops tension and leads to a condition characterized by severe inflammation and edema (MacIntyre, D. L. et al. [2000] supra). Most exercise encountered is concentric/eccentric exercise. Purely eccentrically based exercise is rarely encountered in sports or in activities of daily living. Examples of eccentric exercises are downhill running and eccentric arm exercises, which have been shown to increase neutrophil migration into the skeletal muscle after such injury (Belcastro, A. N. et al. [1996] *J Appl Physiol* 80:1331–5; Camus, G. et al. [1994] supra; Fielding, R. A. et al. [2000] supra; MacIntyre, D. L. et al. [2000] supra). In addition, it appears that eccentric exercise may produce a cellular environment of acute phase inflammation characterized by increases in levels of redox-active metal ions.

The influence eccentric exercise has on some biological markers of inflammation, oxidative stress, and muscle injury has been studied. These markers include, for example, myeloperoxidase, interleuken-6 (IL-6), lactate dehydrogenase (LDH), creatine kinase (CK), myoglobin, and total antioxidant capacity. Some of these investigations examined the effect of particular antioxidant supplements (e.g., vitamins C and E) and specific non-steroidal anti-inflammatory drugs (NSAIDS) on some of these markers before and/or after various degrees of eccentric exercise (Van der Meulen et al. [1997] *J Applied Physiology* 83(3):817–23; Maxwell et al. [1993] *Free Radic Res Commun* 19(3):191–202; Pizza et al. [1999] *Int J Sports Med* 20:–102; Bourgeois et al. [1999] *Med & Science in Sports & Exercise* 31(1):4–9; and Croisier et al. [1996] *Mediators of Inflammation* 5(3):230–4).

Currently, no reliable human or animal model exists to rapidly test substances, such as drugs and natural compounds, for anti-/pro-inflammatory or anti-/pro-oxidant properties. Most substances tested on humans are tested on a specific population suffering from an inflammatory disease condition, e.g., arthritis. Unfortunately, each individual's symptoms are vastly different and responses are highly variable, making objective testing difficult and results unreliable. In addition, there is currently no method for testing such compounds under conditions of acute inflammation characterized by increases in redox-active metal ions. Therefore, it would be advantageous to provide a reliable method for testing a substance on healthy subjects in order to discern the substance's inflammatory and/or oxidant properties under acute inflammatory conditions and/or under conditions of elevated redox-active metal ions.

BRIEF SUMMARY OF THE INVENTION

The subject invention provides methods and systems for testing a substance for inflammatory or oxidant properties. In a preferred embodiment, the method comprises the steps of applying an eccentric exercise stimulus to a subject, thereby inducing a muscle injury in the subject; administering a substance to the subject; measuring at least one biological marker from the subject, wherein the biological marker(s) are selected from the group consisting of inflammatory markers, oxidative stress markers, cell damage markers, and combinations thereof; and correlating the measurements of the biological marker(s) with the inflammatory or oxidant properties of the substance.

The subject invention also provides a system for determining the inflammatory or oxidant properties of a substance comprising sampling means for obtaining a biological sample from a subject; stimulus means for administering eccentric exercise to the subject; analysis means for measuring the amount of at least one biological marker in the biological sample, wherein the biological marker(s) are selected from the group consisting of inflammatory markers, oxidative stress markers, and cell damage markers, or combinations thereof; and means for correlating the measurements of the biological markers with the inflammatory or oxidant properties of the substance.

Advantageously, the muscle injury resulting from the eccentric exercise stimulus induces an acute inflammatory response and causes increased levels of redox-active metal ions within the subject. The method and system of the subject invention can be used to determine if a substance has pro-inflammatory or anti-inflammatory properties, as well as pro-oxidant or antioxidant properties.

The biological marker(s) measured according to the subject invention may be, for example, free iron, total antioxidant status, 8-isoprostane (8-Iso-PGF$_{2\alpha}$), superoxide dismutase (SOD), glutathione peroxidase (GPX), lactate dehydrogenase (LDH), C-reactive protein, lipid hydroperoxidase (LOOH), myeloperoxidase, interleukin-6 (IL-6), creatine kinase (CK), dityrosine, and 8-hydroxyguanine, or combinations thereof. Preferably, the biological marker(s) are selected from the group consisting of free iron, 8-Iso-PGF$_{2\alpha}$, SOD, GPX, dityrosine, and 8-hydroxyguanine, or combinations thereof. More preferably, the biological marker(s) are selected from the group consisting of free iron, 8-Iso-PGF$_{2\alpha}$, SOD, and GPX, or combinations thereof. In a specific embodiment, the biological markers are free iron and/or 8-Iso-PGF$_{2\alpha}$.

The eccentric exercise stimulus applied to the subject may be, for example, an eccentric arm curl exercise, an eccentric leg curl exercise, and a downhill running exercise, or combinations thereof. In a specific embodiment, the eccentric exercise stimulus is applied at between about 60% and about 95% of the subject's maximum intensity. In another embodiment, the eccentric exercise stimulus is applied at between about 70% and about 90% of the subject's maximum intensity. In a further embodiment, the eccentric exercise stimulus is applied at about 80% of the subject's maximum intensity. In another embodiment, the maximum intensity of the eccentric exercise stimulus is the subject's one-repetition maximum weight equivalent (e.g., eccentric press weight, eccentric curl weight, or the magnitude of other force applied to the subject's body), or the subject's maximum heart rate.

DETAILED DISCLOSURE OF THE INVENTION

Figure 1:
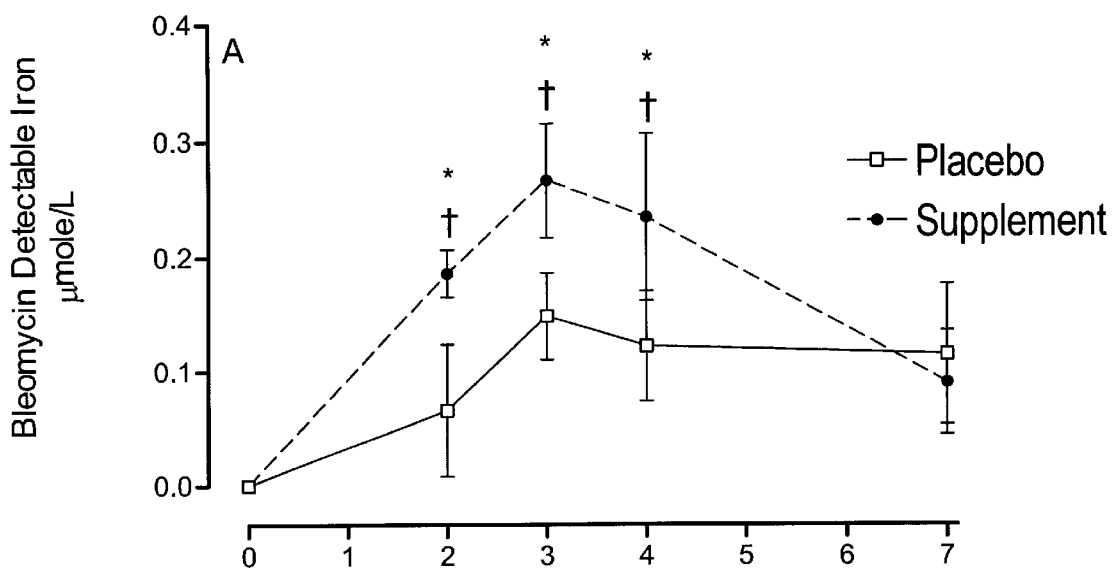
FIG. 1 shows the concentration of bleomycin detectable catalytic iron represented as changes from baseline levels. Subjects received either a placebo (n=7) or an antioxidant supplement (n=7) containing vitamin C (12.5 mg/kg body weight) and n-acetyl cysteine (NAC; 10 mg/kg body weight) for 7 days after an acute muscle injury. The symbol (*) represents a significant difference (p<0.01) from baseline (Day 0) for both placebo and Vit C+NAC group. The symbol (†) represents a significant difference (p<0.0001) between groups. Data is represented as the mean±SEM.

The subject invention provides methods and systems for testing a substance for inflammatory or oxidant properties.

In a preferred embodiment, the method comprises the steps of applying an eccentric exercise stimulus to a subject, thereby inducing a muscle injury in the subject; administering a substance to the subject; measuring one or more biological markers within the subject, wherein the biological marker(s) are selected from the group consisting of inflammatory markers, oxidative stress markers, cell damage markers, and combinations thereof; and correlating the measurements of the biological marker(s) with the inflammatory or oxidant properties of the substance.

The subject invention also provides a system for determining the inflammatory or oxidant properties of a substance comprising sampling means for obtaining a biological sample from a subject; stimulus means for applying eccentric exercise to the subject; analysis means for measuring the amount of one or more biological markers in the biological sample, wherein the biological marker(s) are selected from the group consisting of inflammatory markers, oxidative stress markers, and cell damage markers, or combinations thereof; and means for correlating the measurements of the biological marker(s) with the inflammatory or oxidant properties of the substance.

Advantageously, the muscle injury resulting from the eccentric exercise stimulus induces an acute inflammatory response and causes increased levels of redox-active metal ions within the subject. The method and system of the subject invention can be used to determine if a substance has pro-inflammatory or anti-inflammatory properties, as well as pro-oxidant or antioxidant properties.

The biological marker(s) measured according to the subject invention may be, for example, free iron, total antioxidant status, 8-isoprostane (8-Iso-PGF$_{2\alpha}$), superoxide dismutase (SOD), glutathione peroxidase (GPX), lactate dehydrogenase (LDH), C-reactive protein, lipid hydroperoxidase (LOOH), myeloperoxidase, interleukin-6 (IL-6), creatine kinase (CK), dityrosine, 8-hydroxyguanine, or combinations thereof. Preferably, the biological marker(s) are selected from the group consisting of free iron, 8-Iso-PGF$_{2\alpha}$, SOD, GPX, dityrosine, and 8-hydroxyguanine, or combinations thereof. More preferably, the biological marker(s) are selected from the group consisting of free iron, 8-Iso-PGF$_{2\alpha}$, SOD, and GPX, or combinations thereof. In a specific embodiment, the biological marker is free iron and/or 8-Iso-PGF$_{2\alpha}$.

The eccentric exercise stimulus applied to the subject may be, for example, an eccentric arm curl exercise, an eccentric leg curl exercise, and a downhill running exercise, or combinations thereof. In a specific embodiment, the eccentric exercise stimulus is applied at between about 60% and about 95% of the subject's maximum intensity. In another embodiment, the eccentric exercise stimulus is applied at between about 70% and about 90% of the subject's maximum intensity. In a further embodiment, the eccentric exercise stimulus is applied at about 80% maximum intensity. In another embodiment, the maximum intensity of the eccentric exercise stimulus is the subject's one-repetition maximum weight equivalent (e.g., eccentric press weight, eccentric curl weight, or the magnitude of other force applied to the subject's body), or the subject's maximum heart rate.

In an exemplified embodiment, the means for applying the eccentric exercise stimulus to the subject is an arm curl exercise apparatus. However, the eccentric exercise stimulus of the subject invention can comprise any exercise protocol having an eccentric muscle contraction component, also known as a "negative". An eccentric muscle contraction is one involving forced lengthening of a muscle (or muscle group) as it develops tension. Generally, an eccentric muscle contraction is achieved by applying force to a subject's body while the subject resists the force. Other examples of eccentric exercise stimuli include, but are not limited to, eccentric leg curl exercises and downhill running. Therefore, the eccentric exercise stimulus can comprise concentric/eccentric exercise. In one embodiment, the eccentric exercise stimulus comprises an exercise protocol having a substantially eccentric muscle contraction component. In a further embodiment, the eccentric exercise stimulus comprises an exercise protocol having a purely eccentric muscle contraction component. The eccentric exercise stimulus can be applied to a single muscle, muscles, muscle group, or muscle groups.

The means for providing the eccentric exercise stimulus is preferably a resistance device or apparatus, such as an arm or leg curl machine, a downhill treadmill, or combinations thereof, as these devices tend to provide consistency of movement, duration, resistance, and intensity. Examples of devices that are capable of applying various forms of eccentric exercise include, for example, U.S. Pat. No. 4,765,610; U.S. Pat. No. 4,741,530; and U.S. Pat. No. 5,827,154. However, free weights, elastic rings or bands, or unassisted downhill running could also be used in the practice of the subject invention. The magnitude of the force applied to the subject's body can be constant, or progressively increased or decreased. The force applied to the subject's body can be gravitational. For example, the means for providing the eccentric exercise stimulus can include a plurality of weights, which can be used conjunctively to apply force to the subject's body. The stimulus means can include a mass wherein the magnitude of the force applied to the subject's body can be varied by selectively repositioning all or some of the mass. In another embodiment, the subject's own mass can be used to apply force to the subject's body. In other embodiments, a device such as a ram or winch can be used to apply a force to the subject's body and wherein the device can be driven mechanically, electrically, hydraulically, or otherwise.

Preferably, the eccentric exercise stimulus is applied to the subject until the subject fatigues. The eccentric exercise can include rest periods (e.g., one-minute or two-minute rest periods).

The biological sample is the material being analyzed and is of biological origin. The biological sample can be, for example, blood (serum or plasma), urine, sweat, saliva, interstitial fluid, lymph, or tissue (e.g., biopsy). Measurement of the biological marker(s) can be carried out within the subject or outside of the subject. For example, in one embodiment, a biological sample can be taken and measured within the subject by in-dwelling devices known in the art. Alternatively, a biological sample can be removed from the subject for subsequent measurement of biological marker(s) within the sample. In another embodiment, the biological marker(s) are measured without sequestering a biological sample from its normal environment. For example, in the case of blood, the biological marker(s) can be measured within the blood stream (e.g., in situ), without removing blood from the vessel.

The sampling means can include various devices for collecting biological samples from a subject. Examples of sampling means include, but are not limited to, syringes, catheters, in-dwelling devices (e.g., dialysis probes), and the like. Biological samples can be obtained from various areas of the subject's body. For example, in the case of blood, the sample can be obtained from vascular tissue (e.g., cubital vein) using standard venipuncture methods. Preferably, the biological sample is obtained from an area of the subject's body other than the area to which the eccentric exercise stimulus applied.

In the broader aspects of the subject invention, there are no limitations on the collection and handling of samples, though it is preferable that consistency be maintained. It is preferred to eliminate variations to the extent possible, for example, by taking samples at the same time of day. Other techniques known to those skilled in the art can be utilized to ensure consistency of measurement of analytes in biological samples.

The biological markers utilized in the subject invention, include inflammatory markers, oxidative stress markers, and cell damage markers, or combinations thereof. Inflammatory markers include, but are not limited to, cytokines or other inflammatory mediators that promote the attraction of white blood cells or inflammatory cells. Inflammatory markers can be, but are not necessarily, released from inflammatory cells. Inflammatory markers include, but are not limited to, 8-isoprostane, myeloperoxidase, IL-6, and C-reactive protein. Oxidative stress markers indicate cell damage caused by oxidants or free-radicals. Oxidative stress markers include the radicals and oxidants that reach their respective targets, such as lipids, protein, or DNA, as well as indirect markers of the damage caused by radicals and oxidants. Oxidative stress markers include, but are not limited to, free iron, 8-isoprostane, superoxide dismutase, glutathione peroxidase, lipid hydroperoxidase, dityrosine, and 8-hydroxyguanine. Cell damage markers include biological molecules (e.g., enzymes) wherein their release is associated with necrotic or damaged cells. Cell damage markers include, but are not limited to, creatine kinase and lactate dehydrogenase. Some biological markers can be classified as more than one type of marker. For example, 8-isoprostane can be classified as both an inflammatory marker and an oxidative stress marker.

In one embodiment, the biological markers measured can include at least one inflammatory marker, at least one oxidative stress marker, and at least one cell damage marker. In one embodiment, the biological markers measured include lactate dehydrogenase, dityrosine, and C-reactive protein. Alternatively, the biological markers measured can include combinations thereof. For example, the biological markers measured can include at least one inflammatory marker and at least one oxidative stress marker. In one embodiment, the biological markers measured include 8-isoprostane, myeloperoxidase, and dityrosine. In a further embodiment, the biological markers measured include free iron, IL-6, and 8-hydroxyguanine.

In addition to, or as alternatives to, the assays described in the Examples provided below, other commercial and non-commercial assays can be used as means for measuring the biological marker(s). The assays selected to measure the biological marker(s) within the subject or within the biological sample obtained from the subject can be carried out using a diagnostic kit, for example. The analytic measurements will generally involve contacting the biological sample with one or more reagents so that some detectable change occurs in the sample, which may be related to measurement of the particular biological marker(s), either directly or indirectly. For example, the sample can undergo an optically detectable reaction or other change which results in a change in color, fluorescence, luminescence, or the like, which can be measured by conventional spectrophotometers, fluorometers, light detectors, and the like. In some cases, immunoassays and other specific binding assays can be performed.

Means for measuring the biological marker(s) can include a variety of methods and devices. Typically, a value or level is determined by measuring the marker in a biological sample, such as blood, lymph, saliva, urine, interstitial fluid, tissue, and the like. The measured value can be determined, for example, by enzyme-linked immunosorbent assay (ELISA), immunoassay, enzymatic assay, chromatography, and spectroscopy, or other technique for determining the level of the particular biological marker. The marker can be measured directly or indirectly. The "marker level" or "measured amount" of the marker in the subject, or in the sample obtained from the subject, refers to units of concentration, mass, moles, volume, or other measure indicating the amount of the marker present. The measurement can be "quantitative", where the step of measuring results in the production of a value, which accurately shows the level of the marker in the subject or in the sample obtained from the subject. The measurement can be "semi-quantitative", where the measuring results in the indication of whether the level of the marker is within a particular range. Semi-quantitative methods include, for example, but are not limited to, color indicators or depiction of certain symbols, where each color symbol represents a concentration range. Conventional methods include sending samples of a subject's biological sample to a commercial laboratory for measurement.

In one embodiment, the biological marker(s) are first measured before the application of the eccentric exercise stimulus in order to establish a first value, or baseline value, for comparison to a second value, from a second measurement taken after application of the eccentric exercise stimulus and after administration of the substance.

The measuring means can also include means for recording the measured amount of the biological marker in the sample as a function of the time of occurrence of the eccentric exercise and/or administration of the substance, so as to identify the relationship there between. This can be achieved, for example, through the use of various computer logarithms that record events and/or measurements in relation to time, or in relation to other events and/or measurements.

The concentration of the biological marker in the sample assayed can be correlated with a control value to determine whether the administered substance or substances have a pro-oxidant or antioxidant effect, or a pro-inflammatory or anti-inflammatory effect, under conditions of elevated redox-active metal ions. For example, the difference between a baseline value in a biological marker measured before application of the eccentric exercise stimulus, and the value of the same biological marker measured after application of the eccentric exercise stimulus and after administration of the substance can be determined. This difference can be compared to a control value from another individual (or individuals), wherein the control value is the difference in the values of the same biological marker(s) measured before application of eccentric exercise stimulus and after application of eccentric exercise stimulus, but without administration of the substance (or with administration of a placebo).

The measured values of the biological marker(s) can be compared to the mean or median value for that particular marker (e.g., free iron) in that particular biological sample type (e.g., blood) from other subjects. If the data is pooled with that of other subjects, corrections can be applied according to various differences in the subjects, such as, for example, the subject's weight, age, gender, and/or race.

The control value used for correlating the biological marker values with the inflammatory or oxidant properties of the administered substance can take a variety of forms. It can be a single cut-off value, such as a median or mean. It can be established based upon comparative groups, such as where the biological marker values differ between groups, depending upon parameters such as age, height, weight, race, or gender. The control value can depend upon the particular population selected. For example, an apparently healthy subject can have a different "normal" range of inflammatory markers than a population whose members suffer from an inflammatory disease. Accordingly, the control value selected can take into account the category in which a subject falls. Given the instant disclosure, appropriate ranges and categories can be selected with no more than routine experimentation by those of ordinary skill in the art.

For correlation, the control value can be a single value, multiple values, a single range or multiple ranges. Therefore, in one embodiment, the control value is a plurality of marker level ranges, and the correlation comprises determining in which of the marker level ranges the subject's measured value falls. The substance can then be characterized based on a comparison between the measured value of the biological marker in the subject and the control value. The substance can be characterized, for example, as pro- or anti-inflammatory, and pro- or anti-oxidant, and combinations thereof. A decrease in the level of an inflammatory marker(s) suggests that the substance administered has pro-inflammatory properties. A decrease in the level of an inflammatory marker(s) suggests that the substance administered has anti-inflammatory properties. An increase in the level of an oxidative stress marker(s) suggests that the substance administered has pro-oxidant properties. A decrease in levels of an oxidative stress marker(s) suggests that the substance administered has antioxidant properties. Alternatively, the substance may exhibit no inflammatory or oxidant properties (pro- or anti-).

The substance to be tested can be administered to the subject before, during, or after application of the eccentric exercise stimulus. For example, if the substance is administered before application of the eccentric exercise stimulus, biological marker(s) can be measured and compared to control values to determine if the substance produced a protective or prophylactic effect on the subject.

The substance tested using the method and system of the subject invention can include any substance of interest that can be administered to a subject. The substance tested can be a formulated compound, comprising natural or synthetic ingredients, or a mixture thereof. For example, the substance tested can be an edible food product (e.g., solid, liquid, etc.). The substance can include one or more nutrients, such as amino acids, carbohydrates, lipids, vitamins, and minerals. Examples of vitamins include, but are not limited to, vitamin A (retinal), vitamin $B^1$, (thiamine), vitamin $B^2$ (riboflavin), vitamin $B^6$ (pyridoxine), vitamin $B^{12}$ (cyanocobalamin), vitamin C (ascorbic acid), vitamin D (ergo Calciferol), vitamin E, biotin, folic acid, niacinamide, and pantothenic acid. The substance can include various electrolyte additives. The substance can comprise one or more nutrient supplements, such as phytonutrients.

In addition to previously uncharacterized substances, the substance can include drugs or other substances with known inflammatory and/or known oxidant properties (pro- or anti-), or formulations containing these substances. In this case, the substance is tested using the methods or systems of the subject invention in order to determine inflammatory and oxidant properties under conditions characterized by elevated levels of redox-active metal ions (e.g., iron, copper, etc.).

Examples of known antioxidant agents that can be tested using the subject invention include, but are not limited to, curcumin, trans beta-carotenes, cis beta-carotenes, cis alpha-carotenes, trans lycopenes, cis lycopenes, trans gamma-carotene, cis gamma-carotenes, zeta-carotenes, phytofluene, phytoene, vitamin C, and vitamin E, or combinations thereof The substance can include previously characterized anti-inflammatory agents, such as non-steroidal anti-inflammatory drugs (NSAIDs). Examples of known anti-inflammatory agents that can be tested using the subject invention include, but are not limited to: alclofenac; alclometasone dipropionate; algestone acetonide; alpha amylase; amcinafal; amcinafide; amfenac sodium; amiprilose hydrochloride; anakinra; anirolac; anitrazafen; apazone; balsalazide disodium; bendazac; benoxaprofen; benzydamine hydrochloride; bromelains; broperamole; budesonide; carprofen; cicloprofen; cintazone; cliprofen; clobetasol propionate; clobetasone butyrate; clopirac; cloticasone propionate; cormethasone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; flufenamic acid; flumizole; flunisolide acetate; flunixin; flunixin meglumine; fluocortin butyl; fluorometholone acetate; fluquazone; flurbiprofen; fluretofen; fluticasone propionate; furaprofen; Furobufen; halcinonide; halobetasol propionate; halopredone acetate; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lornoxicam; loteprednol etabonate; meclofenamate sodium; meclofenamic acid; meclorisone dibutyrate; mefenamic acid; mesalamine; meseclazone; methylprednisolone suleptanate; morniflumate; nabumetone; naproxen; naproxen sodium; naproxol; nimazone; olsalazine sodium; orgotein; orpanoxin; oxaprozin; oxyphenbutazone; paranyline hydrochloride; pentosan polysulfate sodium; phenbutazone sodium glycerate; pirfenidone; piroxicam; piroxicam cinnamate; piroxicam olamine; pirprofen; prednazate; prifelone; prodolic acid; proquazone; proxazole; proxazole citrate; rimexolone; romazarit; salcolex; salnacedin; salsalate; salycilates; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triclonide; triflumidate; zidometacin; glucocorticoids; zomepirac sodium, or combinations thereof.

The substance administered to the subject can be formulated for a variety of modes of administration, including systemic and topical or localized administration. The substance can be administered by constant infusion over a period of time. The substance can also be administered in more than one dose. For example, doses can be administered daily. Likewise, measurements of biological marker(s) can be taken after some or all doses.

The dosages of the substance can be administered in a variety of ranges to determine threshold pro-/anti-inflammatory and/or pro-/anti-oxidant properties. For systemic administration, the substance can be ingested orally, or injected by intramuscular, intravenous, intraperitoneal, or subcutaneous routes. Systemic administration can also be by transmucosal or transdermal means.

The subject used in the practice of the subject invention is preferably a mammal. Examples of such mammals include, but are not limited to, mice, rats, rabbits, goats, horse, sheep, cattle, cats, dogs, pigs, monkeys, apes, and humans. More. preferably, the subject is a primate. Most preferably, the subject is human.

Preferably, the subject undergoing the eccentric exercise stimulus, and to which the substance is administered, is not suffering from an inflammatory disease condition or a condition that affects the levels of the particular biological marker being measured. Alternatively, if the subject invention is being used to ascertain the inflammatory or oxidant properties of a substance under conditions associated with a particular disease state (in addition to an acute inflammatory condition characterized by elevated levels of redox-active metal ions), then the subject is preferably suffering from the particular disease state of interest. In a preferred embodiment, the subject is healthy and is non-smoking. "Healthy" subjects include, but are not limited to, those subjects who do not exhibit symptoms of disease. Such subjects, if examined by a medical professional, would be characterized as healthy and free of symptoms of disease. "Non-smoking" subjects include those who, at the time of testing, are not smokers. This includes subjects who have never smoked, as well as subjects who in the past have smoked but presently no longer smoke. Preferably, the subject is not involved in a regular weight-training program and does not have a history of injury to the particular muscle or muscle group to which the eccentric exercise stimulus is applied.

Preferably, the eccentric exercise stimulus is applied to the subject and the biological marker(s) are measured (either within the subject or a sample is taken) when the subject is in a fasting condition. In one embodiment, the subject has fasted from about 6 hours to about 14 hours. In another embodiment, the subject has fasted from about 8 hours to about 12 hours. In a further embodiment, the subject has fasted for about 10 hours.

In one embodiment, the subject has not recently been administered a substance with inflammatory or oxidant properties. Preferably, the subject has not been administered a substance with inflammatory or oxidant properties for a period of about two to six weeks. In another embodiment, the subject has been free of vitamin and/or mineral supplements for a period of about two to about eight weeks.

All patents, patent applications, and publications referred to or cited herein are incorporated by reference in their entirety to the extent they are not inconsistent with the explicit teachings of this specification.

Materials and Methods

Subjects and supplementation. Fourteen healthy males from the University of Florida (24.4±3.6 yr, 178.3±6.5 cm, 78.0±10.8 kg) were recruited for participation in this study. Subjects were free of antioxidant supplementation for six weeks prior to the study. Persons involved in a regular weight-training program or with a prior history of injury to the biceps brachii or elbow region were excluded. This was a double-blind study in which subjects received 12.5-mg vitamin C and 10-mg of NAC per kg body mass in a powdered drink mix. Subjects who received the placebo treatment were given the powdered drink mixture without the antioxidants. The fruit-punch-flavored drink, POWERADE, (Powerade, Atlanta, Ga.) was chosen because it did not contain any supplements. The flavored drink with or without supplements was administered immediately after the eccentric exercise bout and continued each day for 7 days.

Exercise protocol. The CYBEX arm curl machine (Cybex International, Inc., Medway, Mass.) was used for the eccentric exercise protocol. Subjects performed three sets of ten repetitions using 80% of their eccentric 1 repetition maximum using only the non-dominant arm. Subjects were given two-minute rest periods between sets and repetitions were continued until fatigue. Severe pain and edema characterize this type of exercise-induced injury for several days post-injury.

Blood collection. Blood was taken from the cubital vein of the uninvolved arm just before the exercise (Day 0) and on days 2, 3, 4, and 7 following the eccentric injury. Blood was not collected on day 1, since preliminary experiments showed peaks of LDH and CK between days 2 and 4. Blood was collected into VACUTAINER tubes containing ethylenediaminetetraacetic acid ($K_3$EDTA; 8.4 mg/VACUTAINER tube) or into serum collection tubes. Blood was then centrifuged at 4° C. at 1500 g for five minutes. Plasma was allocated to storage tubes containing 100 $\mu$M butylated hydroxytoluene (BHT) and 100 $\mu$M diethylenetriamine pentaacetic acid (DTPA). EDTA serves as a calcium and metal chelator, DTPA serves as a metal chelator, and BHT acts as a chain-breaking antioxidant to prevent lipid peroxidation ex vivo. Samples were stored immediately at −80° C. in multiple aliquots. Experiments show that samples stored during the same time period in the presence of antioxidants had lower baseline levels compared to samples not containing these antioxidants. Samples were stored in multiple aliquots (~0.25 mL) and each sample was thawed only once and immediately analyzed for lipid peroxidation content. This precaution was taken because preliminary experiments showed that samples, which are freeze-thawed even once, showed increases in baseline lipid peroxidation products.

Bleomycin detectable iron. The method of Evans and Halliwell (Evans, P. J. et al. [1994] *Methods Enzymol* 233:82–92) was, used for measurement of bleomycin-detectable iron (BDI) present in the serum. Bleomycin in the presence of ferrous iron degrades DNA to form thiobarbituric acid-reactive product. Degradation by bleomycin is dependent on the concentration of total chelatable redox-active loosely-bound, or "free" iron. Therefore, the rate of degradation of DNA by bleomycin can be used to measure the concentration of catalytic iron in biological fluids.

Total antioxidant status. Total antioxidant status of the serum was measured using methods developed by Randox laboratories (United Kingdom). The method is based on the formation of 2'-2'-Azino-di-[3-ethylbenzthiazoline sulphonate] radical (ATBS*). This has a stable blue-green color, which is measured at 600 nm. The levels of antioxidants in the serum cause a suppression of this color to a degree, which is proportional to their concentration.

Inflammatory markers. To ensure that inflammatory cells were increased in the blood, myeloperoxidase and the cytokine interleukin-6 were measured. Myeloperoxidase was measured using an enzyme-linked immunosorbent assay (ELISA) system (OXIS International, Portland, Oreg.). Interleukin-6 was also determined using an ELISA assay (Endogen Laboratories, Woburn, Mass.).

Enzymatic markers of cell damage. Both creatine kinase (CK-Kit-DG-1340-K) and lactate dehydrogenase (LDH-Kit-DG147-K) were measured spectrophotometrically at 340 nm (SIGMA Chemicals, St. Louis, Mo.).

Non-enzymatic markers of cell damage. Myoglobin was measured using an ELISA (Bethyl Laboratories, Montgomery, Tex.). Human myoglobin was used to establish a standard curve.

Antioxidant enzymes. Superoxide dismutase (SOD) was measured in the serum following the technique described by Oyanagui (Oyanagui, Y. [1984] *Anal Biochem* 142:290–6). Selenium-dependent glutathione peroxidase (GPX) was measured in the serum following the method described by Flohe and Gunzler (Flohe, L. et al. [1984] *Methods Enzymol* 105:114–21) using t-butyl hydrogen peroxide and GSH and NADPH as substrates.

Markers of lipid peroxidation. Lipid hydroperoxides were measured with a spectrophotometric assay from Cayman Chemicals (Ann Arbor, Mich.). Lipid hydroperoxides were extracted into chloroform and detected at 500 nm. Isoprostane was measured by a commercially available EIA kit (Cayman Chemical, Ann Arbor, Mich.). The antibody was highly specific for 8-iso prostaglandin $F_{2\alpha}$ (8-Iso-PGF$_{2\alpha}$), currently classified as 15-$F_{2\alpha}$-IsoP. 8-Iso-PGF$_{2\alpha}$ was measured using an extraction process followed by the ELISA procedure.

Protein determination. Protein concentration was determined using the Bradford method (Bradford, M. M. [1976] *Anal Biochem* 72:248–54).

Statistical Analysis. All analyses were performed in duplicate (mean was used for analysis). A two-way analysis of variance (ANOVA) with repeated measures for the time component of the experiment was performed. Bonferroni post-hoc analysis was used where appropriate. Statistical significance was set at $p<0.05$. Table 2 depicts statistical results of all parameters evaluated. Data was analyzed using a statistical package from Prism (San Diego, Calif.).

Following are examples which illustrate procedures for practicing the invention. These examples should not be construed as limiting. All percentages are by weight and all solvent mixture proportions are by volume unless otherwise noted.

EXAMPLE 1

Serum Catalytic Iron Levels are Increased After Eccentric Injury

The amount of bleomycin detectable iron was measured to determine increases in redox-free iron (Evans, P. J. et al. [1994] *Methods Enzymol* 233:82–92) potentially catalytic for free radical reactions. Bleomycin detectable iron (BDI) was measured in the serum immediately post-exercise (Day 0) and up to seven days following the injury, as shown in FIG. 1. Day 0 indicates blood taken immediately before the eccentric exercise. Levels of BDI were significantly elevated above pre-injury levels in both groups ($p<0.01$) on days 2, 3, and 4. Day 7 showed that levels of BDI returned to baseline. Importantly, FIG. 1 shows that the amount of bleomycin-detectable iron in the serum of supplemented subjects (Vit C+NAC) was significantly higher compared to the placebo group ($p<0.05$). In summary, bleomycin detectable iron increased after the injury and was elevated in the Vit C+NAC group above levels induced by the injury alone.

EXAMPLE 2

Figure 2:
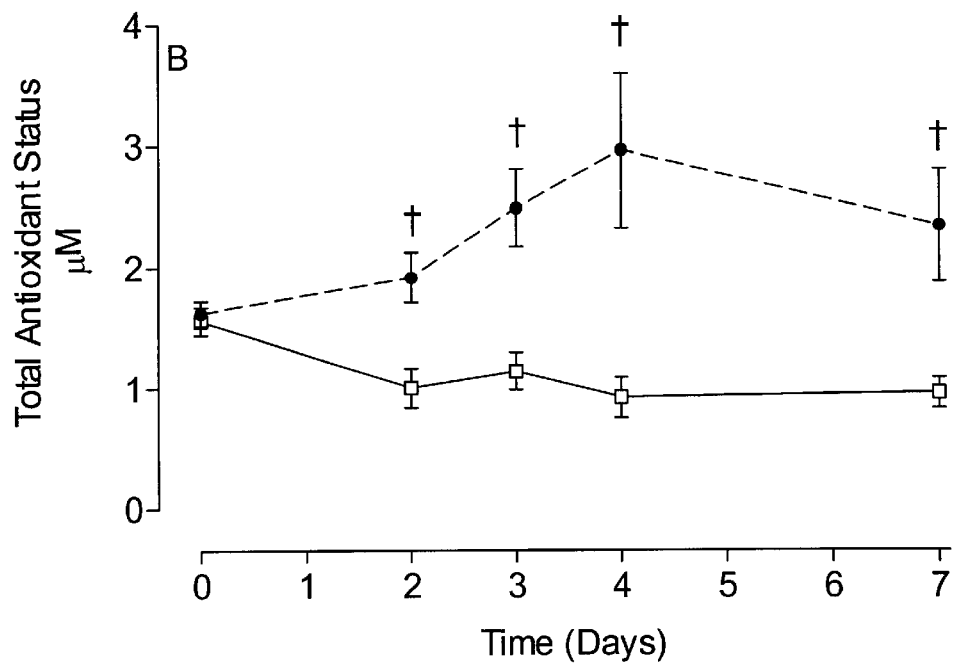
FIG. 2 shows the total antioxidant status in the serum of healthy human volunteers. Subjects received either a placebo (n=7) or an antioxidant supplement (n=7) containing vitamin C (12.5 mg/kg body weight) and n-acetyl cysteine (NAC; 10 mg/kg body weight) for 7 days after an acute muscle injury. The symbol (*) represents a significant difference (p<0.01) from baseline (Day 0) for both placebo and Vit C+NAC group. The symbol (†) represents a significant difference (p<0.0001) between groups. Data is represented as the mean±SEM.

Plasma Total Antioxidant Status is Increased with Vitamin C and NAC Supplementation To test whether the supplements did lead to increased levels of antioxidants in the plasma, total antioxidant status was quantified. Total antioxidant status was measured prior to the injury and for seven days following the eccentric exercise-induced injury. Supplemented subjects showed a significant increase ($p<0.0001$) of their total antioxidant status on days 2, 3, 4, and 7, as shown in FIG. 2. Despite increases in antioxidants, there were still increased levels of markers for oxidative stress in the supplemented group (see following sections). The level of total antioxidants in the placebo group tended to decrease, but this was not statistically significant.

EXAMPLE 3

Markers of Inflammation in the Plasma are Increased After Eccentric Injury

In order to quantify the severity of inflammation and the effects the supplements may have on inflammation, interleukin-6 (IL-6) and plasma myeloperoxidase (MPO) were measured, the levels of which are shown in Table 1. Myeloperoxidase was significantly increased in both treatment groups after the injury, confirming that the injury did stimulate a significant neurtrophilic response. Myeloperoxidase was significantly elevated post-injury on day 2 ($p<0.0001$) in the placebo group and levels did not return to baseline by day 7. The group receiving the supplement also showed a significant increase in MPO on day 2. However, levels were significantly (33%) lower ($p<0.05$) than the placebo group. Also, in contrast, the control subject's MPO levels did return to baseline around day 7. Furthermore, interleukin-6 was significantly elevated in both groups above pre-injury levels on day 2 ($p<0.001$) and returned close to baseline levels by day 7. There were no significant differences in the levels of IL-6 between the placebo and supplemented groups.

TABLE 1

Plasma interleukin-6 and myeloperoxidase levels in human subjects after an eccentric injury receiving either a placebo or Vitamin C and NAC supplement.

|  | Day 0 | Day 2 | Day 7 |
| --- | --- | --- | --- |
| Myeloperoxidase |  |  |  |
| Placebo | 10.8 ± 2.9 | 36.2 ± 4.3* | 17.5 ± 4.1* |
| Vit C + NAC | 8.0 ± 2.8 | 25.2 ± 4.8† | 10.4 ± 3.3† |
| Interleukin-6 |  |  |  |
| Placebo | 1.1 ± 0.16 | 4.4 ± 1.25* | 2.62 ± 0.55* |
| Vit C + NAC | 1.6 ± 0.24 | 4.6 ± 0.63 | 1.97 ± 0.30 |

Mean ± SEM of myeloperoxidase (ng/mL) and interleukin-6 (pg/mL).
*$p < 0.0001$ different from day 0.
†$p < 0.05$ different from placebo.

EXAMPLE 4

Figure 3A:
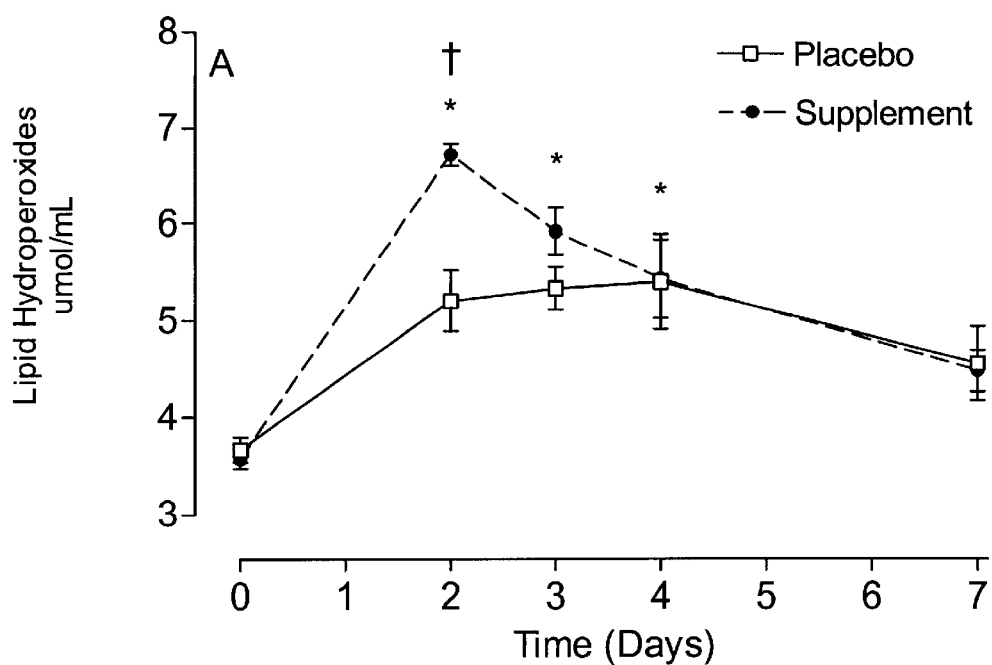
FIGS. 3A and 3B show the levels of plasma lipid hydroperoxides and 8-iso prostaglandin $F_{2\alpha}$ (8-Iso-PGF$_{2\alpha}$), respectively, of healthy human volunteers receiving either a placebo (n=7) or an antioxidant supplement (n=7). The symbol (*) represents a significant difference (p<0.01) from baseline (Day 0) for both placebo and Vit C+NAC group. The symbol (†) represents a significant difference (p<0.0001) between groups. Data is represented as the mean±SEM.
Figure 3B:
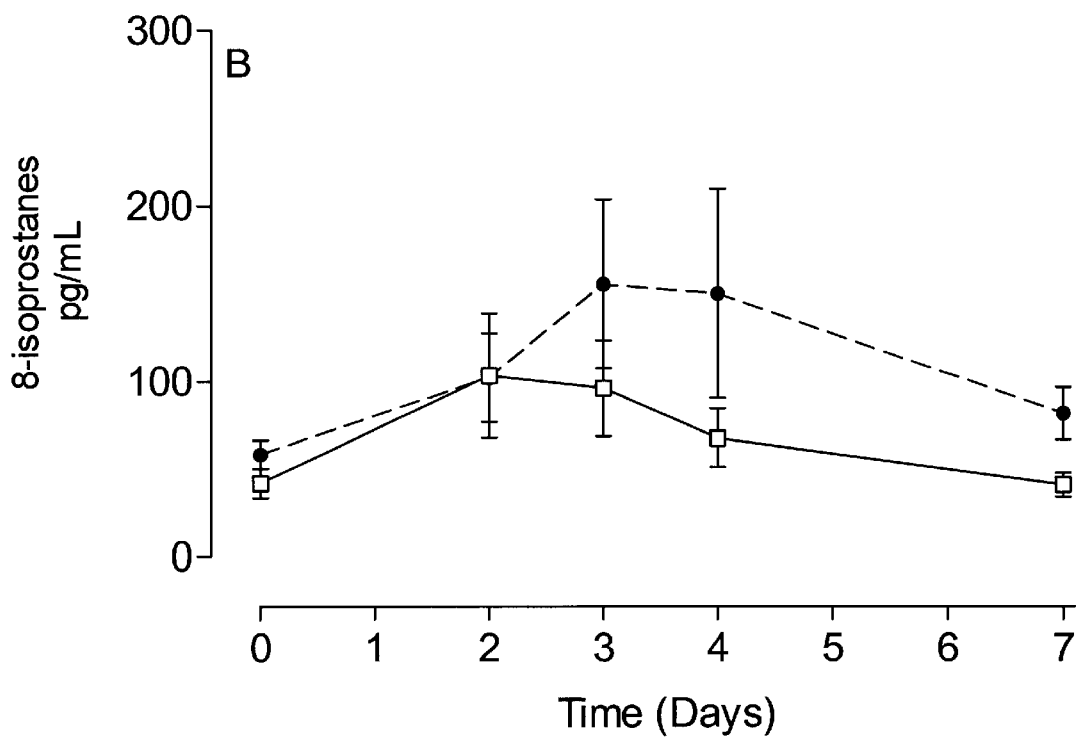

Plasma Markers of Lipid Peroxidation are Elevated in the Vitamin C and NAC group After Eccentric Injury Two markers of lipid oxidation were quantified in the plasma; lipid hydroperoxide (LOOH), and 8-iso prostaglandin $F_{2\alpha}$(8-Iso-PGF$_{2\alpha}$), as shown in FIGS. 3A and 3B, respectively. LOOH is a marker formed in the initial stages of lipid peroxidation and 8-iso PGF$_{2\alpha}$ is a specific marker formed from arachidonic acid oxidation. LOOH levels were significantly elevated post-injury in both groups on days 2, 3, and 4 ($p<0.0001$), as shown in FIG. 3A. Supplementation with Vit C+NAC yielded significantly higher levels of LOOH on days 2 and 3 ($p<0.001$). LOOH levels were not significantly different on day 7 compared to baseline levels (Day 0). 8-iso prostaglandin $F_2\alpha$(8-Iso-PGF$_{2\alpha}$), a member of a family of eicosanoids of non-enzymatic origin and a specific end product of oxidative stress (Morrow, J. D. et al. [1990] *Anal Biochem* 184:1–10), showed a strong trend ($p=0.05$) to be elevated after the injury in both the placebo and vitamin C+NAC group, as shown in FIG. 3B. In addition, vitamin C and NAC supplementation tended to exacerbate the levels of 8-iso PGF$_{2\alpha}$ in the plasma ($p=0.07$). In summary, both markers of lipid peroxidation were elevated with time after the eccentric injury, whereas Vit C+NAC supplementation increased levels of LOOH significantly and 8-Iso-PGF$_{2\alpha}$ also tended to be increased in this group.

EXAMPLE 5

Figure 4A:
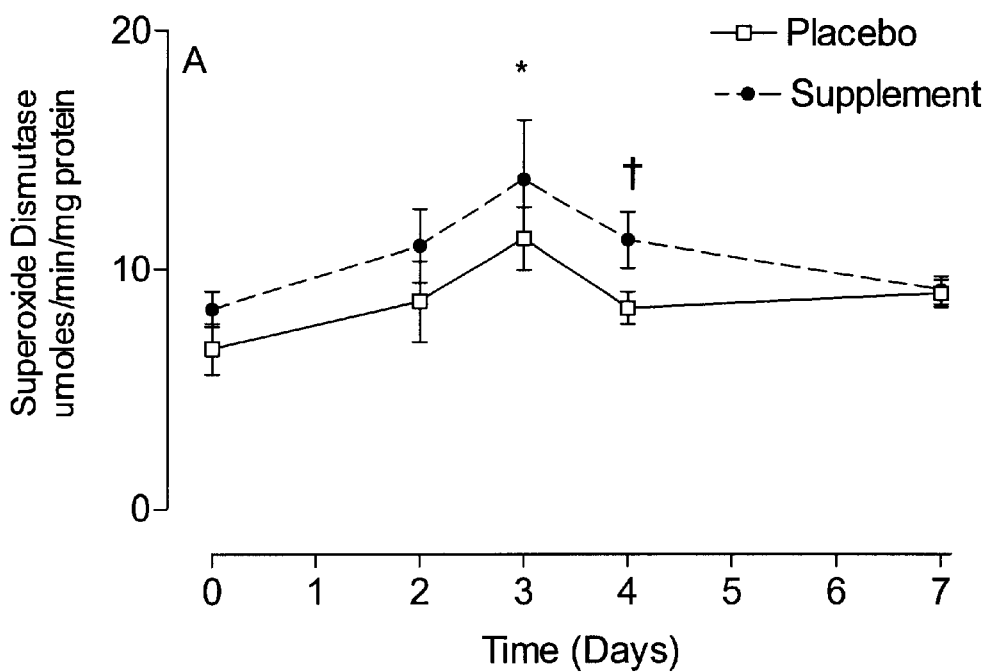
FIGS. 4A and 4B show antioxidant enzymes, superoxide dismutase and glutathione peroxidase, respectively, measured in the serum of healthy human volunteers receiving either a placebo (n=7) or an antioxidant supplement (n=7). The symbol (*) represents a significant difference (p<0.01) from baseline (Day 0) for both placebo and Vit C+NAC group. The symbol (†) represents a significant difference (p<0.0001) between groups. Data is represented as the mean±SEM.
Figure 4B:
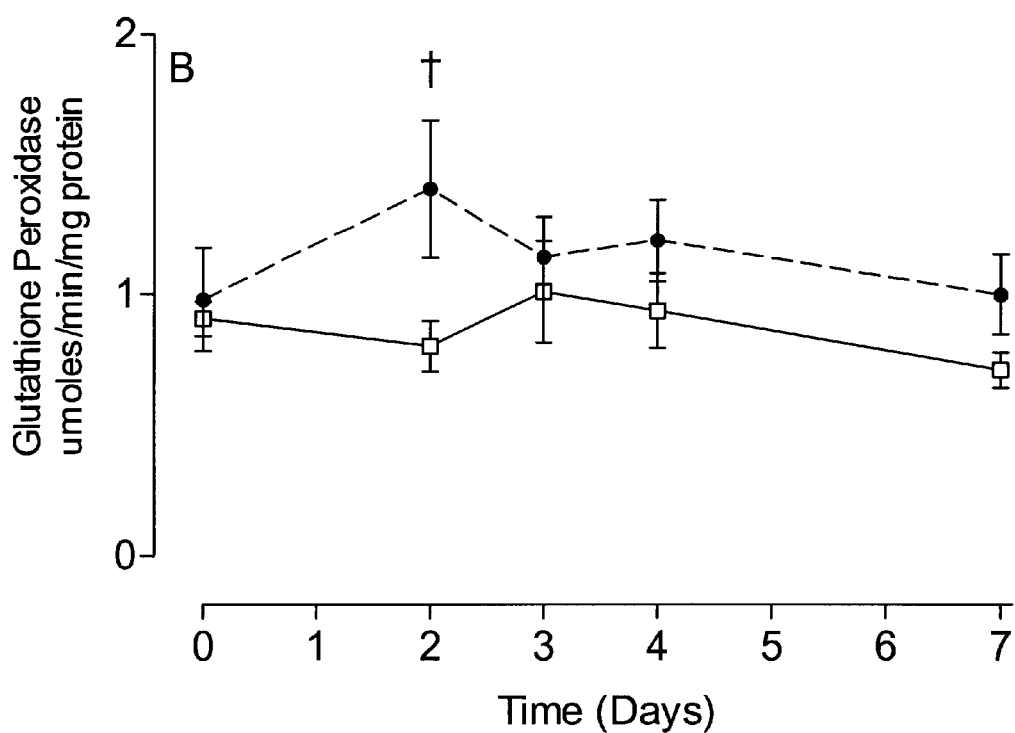

Plasma Antioxidant Enzymes are Elevated in the Vitamin C and NAC Group After the Injury The activity of plasma superoxide dismutase (SOD) and glutathione peroxidase (GPX) were measured because they have been reported to increase after acute exercise and in response to chronic oxidative stress (Leeuwenburgh, C. et al. [1994] *Am J Physiol* 267:R439–45; Leeuwenburgh, C. et al. [1996] *J Nutr* 126:1833–43). As shown in FIG. 4A, plasma SOD activity was significantly elevated in both groups after the injury ($p<0.05$). Furthermore, SOD activity was significantly higher in the group supplemented with vitamin C and NAC ($p<0.05$). As shown in FIG. 4B, plasma GPX activity was not significantly elevated above baseline levels. However, on day two, there were significantly higher activity levels in the supplemented group ($p<0.05$) compared to the placebo group.

EXAMPLE 6

Figure 5A:
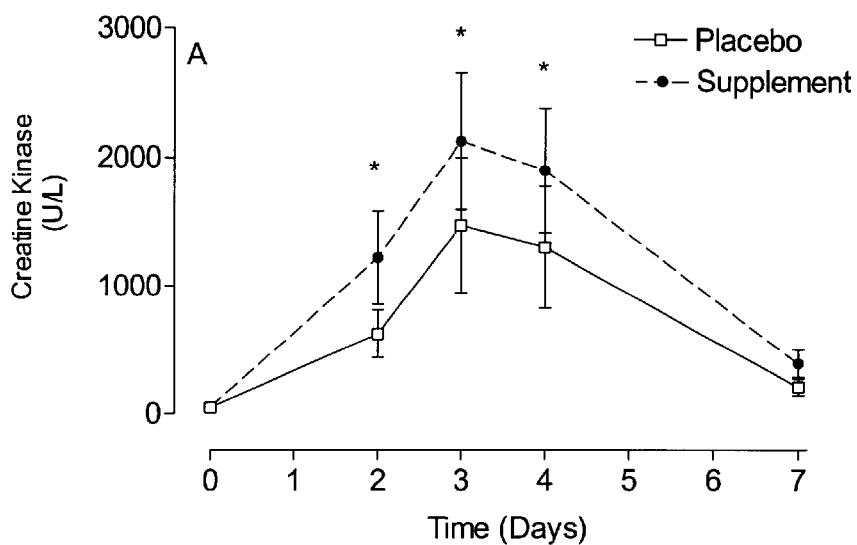
FIGS. 5A, 5B, and 5C show, respectively, the enzymatic markers of cell damage, LDH and CK, and a non-enzymatic marker of cell damage, myoglobin, in the serum of healthy human volunteers. Subjects received either a placebo (n=7) or an antioxidant supplement (n=7). The symbol (*) represents a significant difference (p<0.01) from baseline (Day 0) for both placebo and Vit C+NAC group. The symbol (†) represents a significant difference (p<0.0001) between groups. Data is represented as the mean±SEM.
Figure 5B:
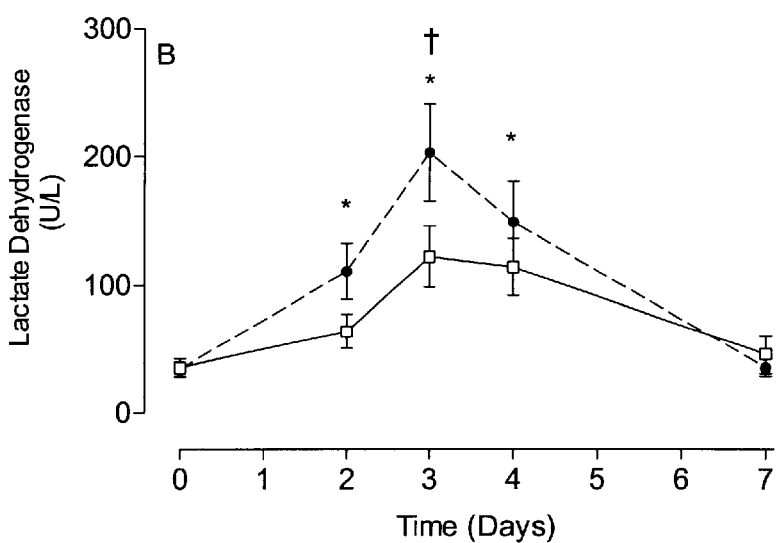
Figure 5C:
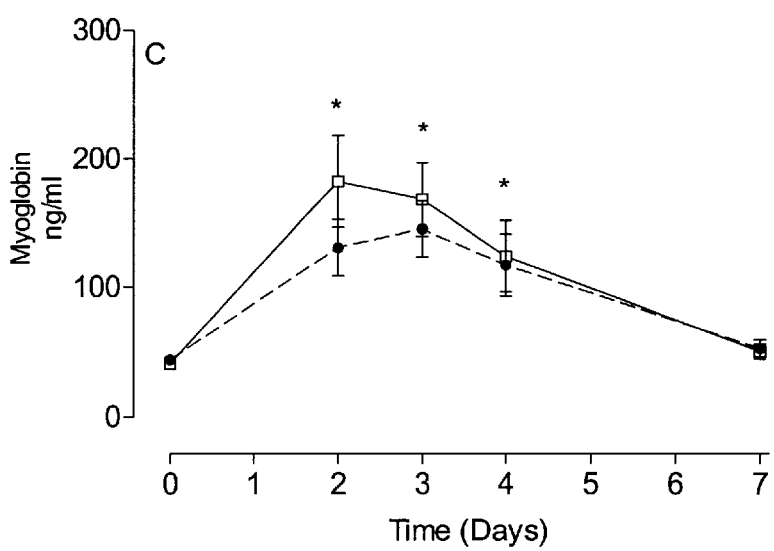

Enzymatic and Non-enzymatic Markers of Cell Damage in the Plasma are Elevated Post-Injury As shown in FIG. 5A, plasma CK was significantly elevated above pre-injury levels in both groups on days 2, 3, and 4 ($p<0.0001$), and tended to increase in the Vit C+NAC group ($p=0.0981$). As shown in FIG. 5B, plasma LDH activity levels in both groups was significantly elevated from pre-injury levels on days 2, 3, and 4 ($p<0.0001$). In addition, the group receiving antioxidant supplementation had significantly higher levels of LDH than the group receiving the placebo treatment ($p=0.0326$). Both CK and LDH returned to baseline values by day 7. Levels of serum myoglobin, a non-enzymatic marker indicative of cell damage, was measured. As shown in FIG. 5C, myoglobin was significantly elevated post-injury in both groups on days 2, 3, and 4 ($p<0.0001$). Levels of myoglobin returned to baseline by day 7 post-injury. In contrast to enzymatic markers of cell damage (CK and LDH), myoglobin tended to be decreased in the supplemented groups ($p=0.13$). Myoglobin's release compared to LDH and CK appears different with vitamin C and NAC supplementation. It may be that this severe injury affected multiple cell types, such as smooth muscle cells, endothelial cells, and muscle cells. Therefore, myoglobin, which is specific for muscle tissue appears to be affected differently from LDH and CK.

TABLE 2

Summary table of statistical analyses of all parameters tested.

| | | Vit. C + NAC vs. Placebo | POST-HOC Vit. C + NAC vs. Placebo DAYS | | | | | Time Effect DAYS | | |
|---|---|---|---|---|---|---|---|---|---|---|
| Measurement | Time | Placebo | 0 | 2 | 3 | 4 | 7 | 2 | 3 | 4 | 7 |
| Antioxidant Capacity | $p = 0.09$ | $p < 0.0001$ | | $p = 0.002$ | $p = 0.001$ | $p = 0.005$ | $p = 0.006$ | | | | |
| Free Iron | $p = 0.0028$ | $p = 0.019$ | | | | | | $p = 0.004$ | $p < 0.001$ | $p = 0.015$ | |
| Lipid Hydroperoxides | $p < 0.0001$ | $p = 0.0006$ | | $p < 0.001$ | $p = 0.04$ | | | $p < 0.001$ | $p < 0.001$ | $p < 0.001$ | |
| 8-Iso-PGF$_{2a}$ | $p = 0.05$ | $p = 0.07$ | | | | | | | | | |
| Superoxide Dismutase | $p = 0.01$ | $p = 0.02$ | | | | $p = 0.02$ | | | | $p < 0.001$ | |
| Glutathione Peroxidase | N/S | $p = 0.01$ | | $p = 0.02$ | | | | | | | |
| Creatine Kinase | $p < 0.0001$ | $p = 0.09$ | | | | | | $p < 0.0001$ | $p < 0.0001$ | $p < 0.0001$ | |
| Lactate Dehydrogenase | $p < 0.0001$ | $p = 0.03$ | | | | | | $p < 0.0001$ | $p < 0.0001$ | $p < 0.0001$ | |
| Myoglobin | $p < 0.0001$ | $p = 0.13$ | | | | | | $p < 0.0001$ | $p < 0.0001$ | $p < 0.0001$ | |
| Interleukin-6 | $p < 0.001$ | N/S | | | | | | $p < 0.001$ | | | |
| Myeloperoxidase | $p < 0.0001$ | $p = 0.050$ | | | | | | $p < 0.001$ | | | |

EXAMPLE 7

Pain and Range of Motion in Injured Arm

Subjective pain perceived by the subjects and the range of motion of the injured arm pre- and post-injury were also assessed. Pain was significantly increased after the injury and peaked after 2 days, but minimal pain was perceived after 7 days. Range of motion of the injured arm was significantly reduced after the injury and returned to similar degrees of range of motion after 7 days. There were no differences between groups in either pain or range of motion assessment. In summary, pain and range of motion were significantly affected after the injury, but the supplement intervention did not affect these basic physiological parameters.

EXAMPLE 8

Dityrosine Isolation and Derivitization

Tyrosine oxidation products, such as dityrosine, can be useful markers of oxidative stress. Isotope dilution gas chromatography-mass spectrometry (GC/MS) is a combination of techniques that can be used to protein oxidation by quantifying specific unnatural amino acids that appear when oxidants modify the corresponding natural amino acids. These oxidized amino acids, such as dityrosine, are stable and GC/MS can be used to detect trace amounts.

Amino acids were isolated using solid C-18 columns (3 mL; SUPERCLEAN SPE; Supelco, Inc., Pa.). First, one mL of urine was supplemented with 10% (v/v) trichloroacetic acid and centrifuged at 14,000 rpm for 5 minutes in an Eppendorf microfuge. The column was conditioned with 2 mL of methanol, 6 mL of 50 mM NaHPO$_4$ (pH 7.4) containing 0.1 mM DTPA, and finally with 6 mL of 0.1% trifluoroacetic acid. Approximately 0.5 mL of the 0.1% trifluroacetic acid remained on the column. Urine (0.5 mL) was then added to the column supplemented with 10% (v/v) trichloroacetic acid and the $^{13}$C-labeled internal standards. Samples were passed onto the column and then the column was washed with 6 mL of 0.1% trifluoroacetic acid. The amino acids were eluted with 2 mL of 25% methanol and dried under vacuum for derivatization.

Amino acids were converted to n-propyl esters by the addition of 200 μl HCl/n-propanol (1 :3, v/v) and heating for 1 hour at 65° C. After evaporation of excess reagent under N$_2$, heptafluorobutyric anhydride/ethyl acetate (1:3, v/v) was added. Samples were heated at 65° C. for 15 minutes.

Amino acids, including dityrosine, were quantified using stable isotope dilution negative-ion chemical-ionization gas chromatography mass spectrometry. Samples were dried under N$_2$, re-dissolved in 100 μl ethyl acetate, and 1 μl aliquots were then analyzed on a Hewlett Packard 5890 gas chromatograph equipped with a 12 m DB-1 capillary column (0.200 mm id, 0.33 micron film thickness, J &W Scientific) interfaced with a Hewlett Packard 5988A mass spectrometer with extended mass range. Full scan mass spectra and selected ion monitoring data were obtained from the n-propyl-heptafluorobutyryl derivatives of both authentic and $^3$C-labeled amino acids in the NCI mode, with methane as the reagent gas.

EXAMPLE 9

8-Hydroxyguanine and C-Reactive Protein 8-hydroxyguanine (8-oxo-dG) is a direct marker of oxidative DNA damage and, hence, an indirect marker of oxidative stress in cells. Specifically, 8-hydroxyguanine is a pre-mutagenic DNA adduct (mainly G:C to T:A transitions) formed by free radical oxygen species, such as hydrogen peroxide. The 8-hydroxyguanine lesion occurs at the N7-C8 bond of guanine and is a common form of base change caused by oxidative stress.

The 8-hydroxyguanine marker can be detected and quantified in a variety of ways. For example, an anti-8-hydroxyguanine antibody can be utilized as part of an immunoassay, such as an enzyme-linked immunosorbent assay (ELISA). An anti-8-hydroxyguanine monoclonal antibody is available from TREVIGEN (Trevigen, Inc., Gaithersburg, Md.), product number 4355-MC-100

C-reactive protein is an inflammatory marker that is released from liver during episodes of inflammation. Studies have shown a positive correlation between C-reactive protein and coronary artery disease (Mendall M. A. et al. [1996]

BMJ 312:1061–1065). C-reactive protein can be detected and quantified in a variety of ways. For example, an anti-C-reactive protein antibody can be utilized as part of an immunoassay, such as an ELISA. Anti-C-reactive protein antibodies are available from Alpha Diagnostic International (San Antonio, Tex.) and BIODESIGN (BioDesign International, Saco, Me.).

Briefly, the antibody is immobilized on an inert solid support, such as polystyrene. In the case of 8-hydroxyguanine, for example, the biological sample (e.g., blood) being assayed is contacted with the antibody-coated surface under conditions which the antibody binds the 8-hydroxyguanine within the sample and the unbound antigen is then washed away. The resulting 8-hydroxyguanine-antibody complex is further reacted with a second antibody to which an easily assayed enzyme has been covalently linked. After washing away any unbound antibody-linked enzyme, the enzyme in the immobilized antibody-8-hydroxyguanine-antibody-enzyme complex is measured (e.g., spectrophotometrically), thereby indicating the amount of 8-hydroxyguanine present in the sample. Alternatively, a radio-immunoassay could be carried out using the anti-8-hydroxyguanine antibody.

It should be understood that the examples and embodiments described herein are for illustrative purposes only and that modifications or changes in light thereof will be suggested to persons skilled in the art and are included within the spirit and purview of this application.

What is claimed is:

1. A method for screening a substance for inflammatory or oxidant properties comprising:
   (a) applying an eccentric exercise stimulus to a subject, thereby inducing a muscle injury in the subject;
   (b) administering a substance to the subject;
   (c) measuring at least one biological marker from said subject to obtain a value of said biological marker, wherein said biological marker is selected from the group consisting of free iron, total antioxidant status, 8-isoprostane, superoxide dismutase, glutathione peroxidase, lactate dehydrogenase, C-reactive protein, lipid hydroperoxidase, myeloperoxidase, interleukin-6, dityrosine, and 8-hydroxyguanine; and
   (d) correlating the measured value of said biological marker with the inflammatory or oxidant properties of said substance.

2. The method according to claim 1, wherein said muscle injury resulting from said eccentric exercise stimulus induces an acute inflammatory response causing increased levels of redox-active metal ions.

3. The method according to claim 1, wherein free iron is measured.

4. The method according to claim 1, wherein total antioxidant status is measured.

5. The method according to claim 1, wherein 8-isoprostane is measured.

6. The method according to claim 1, wherein superoxide dismutase is measured.

7. The method according to claim 1, wherein glutathione peroxidase is measured.

8. The method according to claim 1, wherein lactate dehydrogenase is measured.

9. The method according to claim 1, wherein C-reactive protein is measured.

10. The method according to claim 1, wherein lipid hydroperoxidase is measured.

11. The method according to claim 1, wherein myeloperoxidase is measured.

12. The method according to claim 1, wherein interleukin-6 is measured.

13. The method according to claim 1, wherein dityrosine is measured.

14. The method according to claim 1, wherein 8-hydroxyguanine is measured.

15. The method according to claim 1, wherein said biological marker is selected from the group consisting of free iron and 8-isoprostane.

16. The method according to claim 1, wherein 8-isoprostane, myeloperoxidase, and dityrosine are measured.

17. The method according to claim 1, wherein lactate dehydrogenase, dityrosine, and C-reactive protein are measured.

18. The method according to claim 1 wherein free iron, interleukin-6, and 8-hydroxyguanine are measured.

19. The method according to claim 1, wherein said eccentric exercise stimulus is selected from the group consisting of eccentric arm curl exercises, eccentric leg curl exercises, and downhill running exercises.

20. The method according to claim 1, wherein said eccentric exercise stimulus is applied to the subject at between about 60% and about 95% maximum intensity.

21. The method according to claim 20, wherein said maximum intensity of said eccentric exercise stimulus is selected from the group consisting of the subject's one repetition maximum weight equivalent and the subject's maximum heart rate.

22. The method according to claim 1, wherein said eccentric exercise stimulus is applied to the subject at between about 70% and about 90% maximum intensity.

23. The method according to claim 1, wherein the measuring step comprises taking a first biological sample from the subject before said eccentric exercise stimulus, taking a second biological sample after said eccentric exercise stimulus and after said substance administration, and measuring said biological marker in said first and second biological samples.

24. The method according to claim 23, wherein said correlating step comprises comparing the measured value of said biological marker in said first sample with the measured value of said biological marker in said second sample.

25. The method according to claim 1, wherein said correlating step further comprises comparing the measured value of said biological marker with a control value.

26. The method according to claim 25, wherein said control value comprises a measured value of the same biological marker from a different subject, wherein said eccentric exercise stimulus has been applied to the different subject, but wherein the different subject has not been administered said substance.

27. The method according to claim 1, wherein said substance administration is carried out after said application of eccentric exercise stimulus; and said measuring is carried out at least twice, including before said application of eccentric exercise stimulus and after said application of eccentric exercise stimulus.

28. The method according to claim 1, wherein said subject is a mammal.

29. A method for screening a substance for inflammatory or oxidant properties comprising:
   (a) applying an eccentric exercise stimulus to a subject, thereby inducing a muscle injury in the subject;
   (b) administering a substance to the subject;
   (c) measuring at least one oxidative stress marker from said subject to obtain a value of said oxidative stress marker; and (d) correlating the measured value of said oxidative stress marker with the inflammatory or oxidant properties of said substance.

30. The method according to claim 29, wherein said oxidative stress marker is selected from the group consisting of free iron, 8-isoprostane, superoxide dismutase, glutathione peroxidase, dityrosine, and 8-hydroxyguanine.

31. A method for screening a substance for inflammatory or oxidant properties comprising:
   (a) applying an eccentric exercise stimulus to a subject, thereby inducing a muscle injury in the subject, wherein the muscle injury causes an acute inflammatory response characterized by an increase in redox-active metal ions;
   (b) administering a substance to the subject;
   (c) measuring biological markers within the subject to obtain a value of the biological markers, wherein the biological markers include at least one inflammatory marker selected from the group consisting of 8-isoprostane, myeloperoxidase, interleukin-6, and C-reactive protein, and at least one oxidative stress marker selected from the group consisting of free iron, superoxide dismutase, glutathione peroxidase, lipid hydroperoxidase, dityrosine, and 8-hydroxyguanine, wherein said measuring comprises taking a first biological sample from the subject before said eccentric exercise stimulus, taking a second biological sample after said eccentric exercise stimulus and after said substance administration, and measuring said biological markers in said first and second biological samples; and
   (d) correlating the measured values of the biological markers with the inflammatory or oxidant properties of the substance, wherein said correlating comprises comparing the measured value of the biological markers in the first sample with the measured value of the biological markers in the second sample to determine if said measured values increase, decrease, or remain the same.

32. A method for screening a substance for inflammatory or oxidant properties comprising:
   (a) applying an eccentric exercise stimulus to a subject, thereby inducing a muscle injury in the subject, wherein the muscle injury causes an acute inflammatory response characterized by an increase in redox-active metal ions;
   (b) administering a substance to the subject;
   (c) measuring 8-isoprostane within the subject to obtain a value of said 8-isoprostane, wherein said measuring comprises taking a first biological sample from the subject before said eccentric exercise stimulus, taking a second biological sample after said eccentric exercise stimulus and after said substance administration, and measuring said 8-isoprostane in said first and second biological samples; and
   (d) correlating the measured value of the 8-isoprostane with the inflammatory or oxidant properties of the substance, wherein said correlating comprises comparing the measured value of said 8-isoprostane in the first sample with the measured value of the 8-isoprostane in the second sample to determine if said measured values increase, decrease, or remain the same.

33. A system for determining the inflammatory or oxidant properties of a substance comprising:
   (a) a sampling means for taking a biological sample from a subject;
   (b) a stimulus means for applying eccentric exercise to the subject before, during, or after a substance has been administered to the subject; and
   (c) a measuring means for measuring the amount of at least one biological marker in the biological sample, wherein the biological marker is selected from the group consisting of free iron, total antioxidant status, 8-isoprostane, superoxide dismutase, glutathione peroxidase, lactate dehydrogenase, C-reactive protein, lipid hydroperoxidase, myeloperoxidase, interleukin-6, dityrosine, and 8-hydroxyguanine.

34. The system according to claim 33, wherein said system further comprises:
   (d) a correlating means for correlating the measured amounts of the biological marker with the inflammatory or oxidant properties of the substance.

35. The system according to claim 33, wherein the biological marker is selected from the group consisting of free iron and 8-isoprostane.

36. The system according to claim 33, wherein 8-isoprostane, myeloperoxidase, and dityrosine are measured.

37. The system according to claim 33, wherein lactate dehydrogenase, dityrosine, and C-reactive protein are measured.

38. The system according to claim 33, wherein free iron, interleukin-6, and 8-hydroxyguanine are measured.

39. The system according to claim 33, wherein said measuring means further comprises means for recording the measured amount of the biological marker in the sample as a function of the time of occurrence of the eccentric exercise, so as to identify the relationship there between.

40. The system according to claim 33, wherein the biological sample is a blood sample.

41. The system according to claim 33, wherein said stimulus means induces an acute inflammatory injury in the subject and wherein the injury causes an increase in redox-active metal ions in the subject.

42. The system according to claim 33, wherein said eccentric exercise is selected from the group consisting of eccentric arm curl exercises, eccentric leg curl exercises, and downhill running exercises.

43. The system, according to claim 33, wherein said correlating means comprises means for comparing the measured amounts of the biological marker with a control value.

44. A system for determining the inflammatory or oxidant properties of a substance comprising:
   (e) a sampling means for taking a biological sample from a subject;
   (f) a stimulus means for applying eccentric exercise to the subject before, during, or after a substance has been administered to the subject; and
   (g) a measuring means for measuring the amount of at least one oxidative stress marker in the biological sample.

45. The system according to claim 44, wherein the oxidative stress marker is selected from the group consisting of free iron, 8-isoprostane, superoxide dismutase, glutathione peroxidase, dityrosine, and 8-hydroxyguanine.

* * * * *

UNITED STATES PATENT AND TRADEMARK OFFICE
CERTIFICATE OF CORRECTION

PATENT NO.   : 6,541,265 B2
DATED        : April 1, 2003
INVENTOR(S)  : Christiaan Leeuwenburgh It is certified that error appears in the above-identified patent and that said Letters Patent is hereby corrected as shown below:

Column 2,
Line 40, "ascorbate" should read -- ascorbate˙ --.

Column 3,
Line 5, "study protective" should read -- study showed the protective --.

Column 13,
Line 37, "was, used" should read -- was used --.

Column 16,
Line 2, "$F_2\alpha$" should read -- $F_{2\alpha}$ --.

Column 18,
Line 42, "$^3$C-labeled" should read -- $^{13}$C-labeled --.

Signed and Sealed this

Seventh Day of October, 2003

JAMES E. ROGAN
*Director of the United States Patent and Trademark Office*